(12) United States Patent
Hiatt

(10) Patent No.: US 7,157,284 B2
(45) Date of Patent: Jan. 2, 2007

(54) VACUUM DISTILLATION AUTOMATIC SAMPLER

(75) Inventor: Michael Howard Hiatt, Las Vegas, NV (US)

(73) Assignee: The United States of America as represented by the Environmental Protection Agency, Washington, DC (US)

( * ) Notice: Subject to any disclaimer, the term of this patent is extended or adjusted under 35 U.S.C. 154(b) by 758 days.

(21) Appl. No.: 10/279,907

(22) Filed: Oct. 25, 2002

(65) Prior Publication Data

US 2003/0064520 A1 Apr. 3, 2003

Related U.S. Application Data

(62) Division of application No. 09/697,046, filed on Oct. 27, 2000.

(60) Provisional application No. 60/162,206, filed on Oct. 29, 1999.

(51) Int. Cl.
  *G01N 35/00* (2006.01)
  *G01N 1/10* (2006.01)
  *G01N 1/22* (2006.01)
(52) U.S. Cl. .................. 436/43; 180/181; 180/158; 422/68.1; 422/83; 422/62
(58) Field of Classification Search ............ 436/180, 436/43, 52, 158, 177, 181; 422/68.1, 83, 422/62, 63
See application file for complete search history.

(56) References Cited

U.S. PATENT DOCUMENTS

| 2,153,105 | A | 4/1939 | Szecsi |
| 4,022,592 | A | 5/1977 | Saaski |
| 4,231,990 | A | 11/1980 | Jottier |
| 4,461,328 | A | 7/1984 | Kenney |
| 4,480,039 | A | 10/1984 | Closmann et al. |
| 4,600,559 | A | 7/1986 | Hiatt |
| 4,980,130 | A | 12/1990 | Metzger et al. |
| 5,024,952 | A | 6/1991 | Alsop |
| 5,411,707 | A | 5/1995 | Hiatt |
| 5,730,938 | A | 3/1998 | Carbonari et al. |
| 5,741,708 | A | 4/1998 | Carey et al. |
| 6,033,628 | A | 3/2000 | Kaltenbach et al. |
| 6,063,634 | A | 5/2000 | Chomka et al. |
| 6,132,582 | A | 10/2000 | King et al. |
| 6,146,595 | A | 11/2000 | Mikulsky |
| 6,235,175 | B1 | 5/2001 | Dubrow et al. |
| 6,264,892 | B1 | 7/2001 | Kaltenbach et al. |

*Primary Examiner*—Brian R. Gordon
(74) *Attorney, Agent, or Firm*—Browdy and Neimark, PLLC

(57) ABSTRACT

A plurality of samples can be analyzed sequentially in any desired order by intruding the samples into an automatic sampler, the automatic sampler including a plurality of sample ports connected to a holder, a connector, a valve, and a seal. The connector if each sample holder is attached to the valve by a transfer line, and each sample port is connected to a common manifold. A vacuum pump is activated to volatilize the samples sequentially through the common manifold to a vacuum distiller. The order of the samples volatilized is controlled by a microprocessor. Once the sample has been volatilized, the vapors are condensed and sent to an analytical device.

10 Claims, 2 Drawing Sheets

VACUUM DISTILLATION AUTOMATIC SAMPLER

CROSS-REFERENCE TO RELATED APPLICATIONS

The present application is a divisional of Ser. No. 09/697,046, filed Oct. 27, 2000, which the non-provisional application of Ser. No. 60/162,206, filed Oct. 29, 1999, the entire contents of which are hereby incorporated by reference.

FIELD OF THE INVENTION

The present invention is directed to an automatic sampler for vacuum extractors for analyzing samples for volatile organic compounds. The apparatus for the present invention makes it possible to analyze a series of samples unattended.

BACKGROUND OF THE INVENTION

In recent years there has been a growing concern over exposure to toxins in the environment and the food supply. The Federal Water Pollution Control Act Amendments of 1972 (PL 92–500) recognized the need for monitoring and establishing the presence of toxic substances in water. Organic pollutants are frequently present in very small amounts, and often comprise a large number of similar compounds which may have been deposited at a particular location by a variety of means. Some of these pollutants are concentrated in the tissues plants and animals, and can be hazardous to these life forms as well as to the animals, including humans, that eat them. Thus it is important top be able to measure accurately trace amounts of contaminating pollutants.

While conventional chromatography and detection techniques are effective measurers and detectors of organic compounds, the samples to be tested contain the organic compound components in matrices or are in matrices which may interfere with the proper extraction and detection of the compound components to be detected. Using conventional techniques, it has been difficult to determine certain compounds, to assess the degree of matrix effects on compound recovery, and to quantify accurately the amounts of these and other compounds.

Soil, biological samples, oils, and water each present unique difficulties and interfering chemicals. Techniques prior to, and even after, the vacuum extractor described in applicant's earlier U.S. Pat. No. 4,600,599, have not been particularly effective in detecting an accurate amount of chemicals in certain types of samples because of low rates of extraction and poor separation.

Prior investigators have attempted to measure trace organic compounds by a number of techniques. One method is to sample gas from the head space above a sample in a closed container. The gas sample is then injected into a gas chromatograph for measurement. Details and variations on this technique are described in references cited in Hiatt, U.S. Pat. No. 5,411,707, the entire contents of which are hereby incorporated by reference.

Other methods for measuring trace organic chemicals which have not been entirely successful include pentane extraction of organic compounds from fish, or the purge and trap method.

Some of the problems with heating a sample and trapping the released compounds have been ameliorated by using a vacuum rather than heat to extract compounds. Improvements in the purge and trap method have been described by Hiatt in *Analytical Chemistry*, 55: 506–516 (1983) and Hiatt, U.S. Pat. No. 4,600,599.

Further improvements in these methods are provided in Hiatt, U.S. Pat. No. 5,411,707. This system detects and measures low concentrations of distillable substances using vacuum distillation in which water and other compounds are removed by a condenser, and gases recollected in a cryogenic concentrator connected to at least one gas chromatograph/mass spectrometer or other analytic detector, such as atomic adsorption, HPLC, ICP, SCFE, and the like. This device is capable of analyzing one sample accurately by the standard methods. However, each analysis must be followed by an operator's intervention to remove the sample container holding residue from the distilled sample, and then attaching a new sample for distilling. This one sample at a time process requires an operator to stand by, and therefore, it is not efficient for production analyses.

SUMMARY OF THE INVENTION

It is an object of the present invention to overcome the aforesaid deficiencies of the prior art.

It is another object of the present invention to provide an automatic sampler that can be used with an analyzer for analysis of a plurality of samples.

It is another object of the present invention to provide a device for performing sequential analyses which can be controlled by a conventional microprocessor.

It is still another object of the present invention to provide an automatic sampler for use in sample analysis in which the potential for contamination from one sample to another sample is negligible.

According to the present invention, an automatic sampler is provided for an analytical device such as a vacuum distiller such as described in U.S. Pat. No. 5,411,707, which is controlled by an external conventional microprocessor. Vapors distilled from samples are transferred from the automatic sampler to the vacuum distiller or other analytical device by a vacuum supplied by a vacuum pump that is a component of the analytical device. Using the microprocessor of the analytical device and vacuum pump greatly simplifies the design and cost of the automatic sampler of this invention.

DETAILED DESCRIPTION OF THE INVENTION

Figure 1:
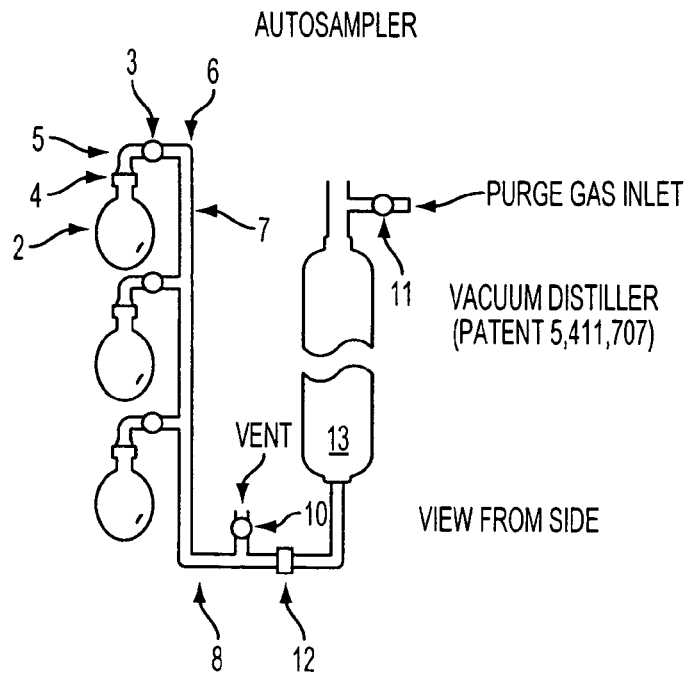
FIG. 1 shows a side view of the automatic sampler of the present invention.
Figure 2:
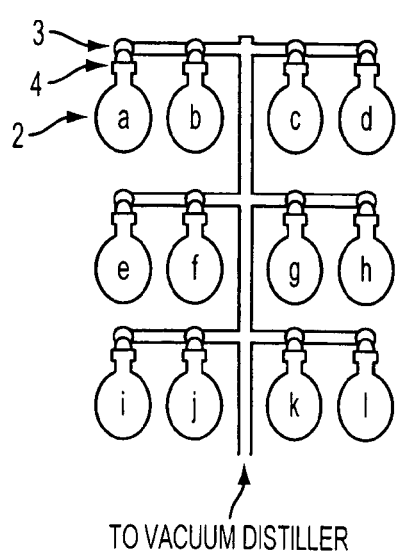
FIG. 2 shows a front view of the automatic sampler of the present invention.
Figure 3:
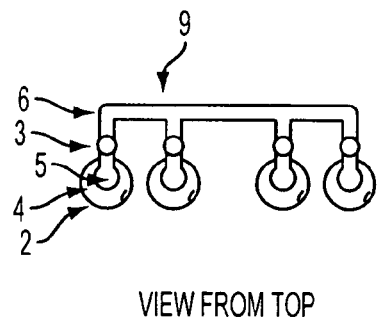
FIG. 3 shows a top view of the automatic sampler of the present invention.

Referring to the figures, the automatic sampler consists of 12 sample ports, labeled a to 1 in the figures. Each port contains: a sample in a glass round bottom flask 2, with an O-ring connector, a solenoid valve (e.g., model 52J8DGB, Peter Paul electronics Co., Inc. New Britain, Conn.) 3, and an O-ring seal. Each O-ring connector of flask 2 is attached to the solenoid valve 3 by a transfer line which is preferably ¼ inch in diameter and made of stainless steel. All of the lengths of tubing are optionally lined with fused silica. Each sample port a through 1 is connected to a common manifold 7 by tubing 6 which is preferably stainless steel and has a diameter of e.g., ¼ inch. The common manifold 7 is then attached to the vacuum distiller by tubing 8. The automatic samples manifold is a vertical tube that connects three horizontal tiers of sample ports. All tubing and valve connections were constructed using compression or NPT fittings.

Figure 4:
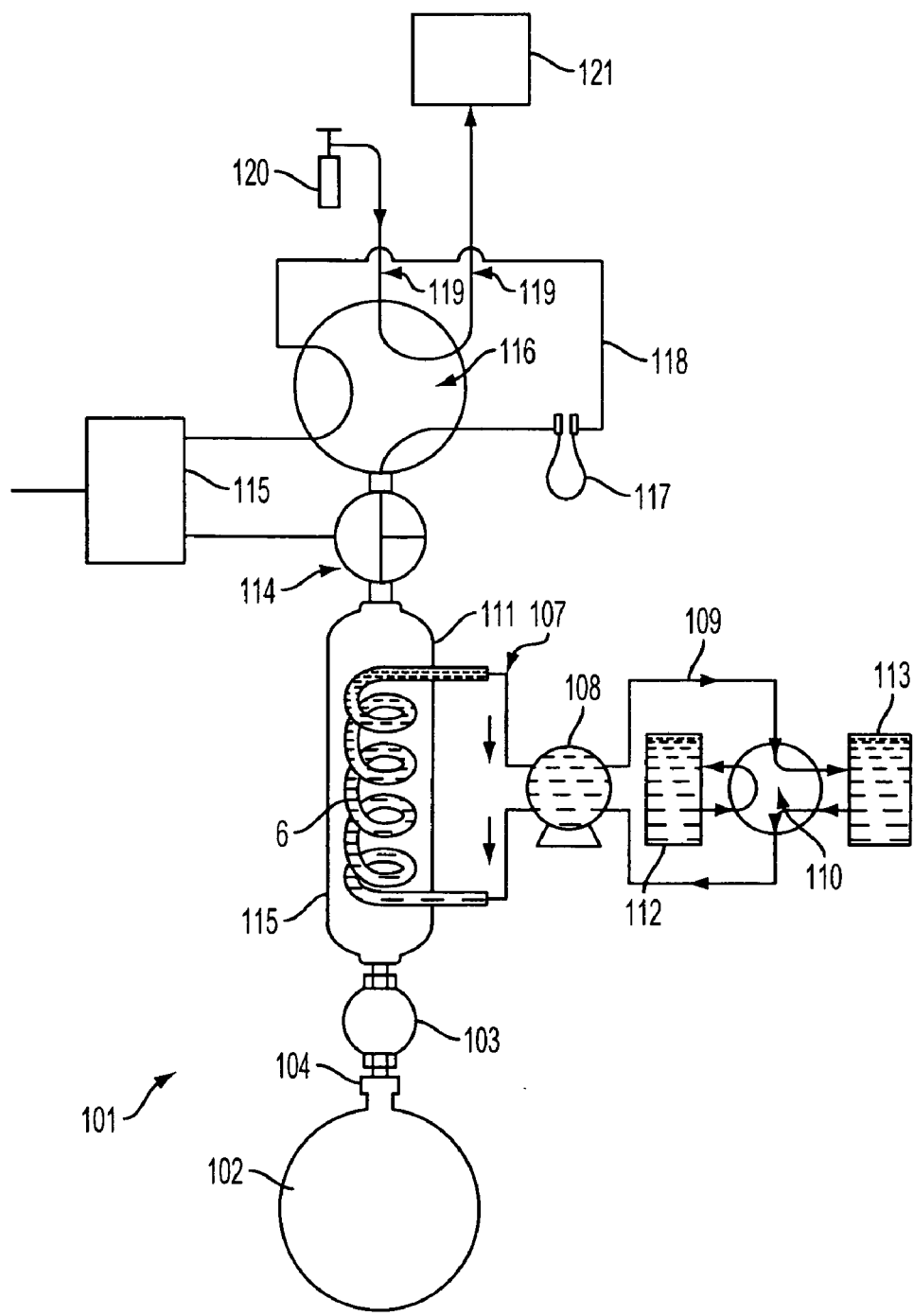
FIG. 4 shows the vacuum distiller of U.S. Pat. No. 5,411,707.

As shown in FIG. 4, the vacuum distiller of U.S. Pat. No. 5,411,707 was modified to connect to the automatic samples and to allow a routine for decontaminating the automatic sampler. Three changes to the vacuum distiller were the replacement of the vacuum distiller's sample chamber with a connection 12, a vent line attached to a solenoid valve 10, and a purge gas inlet line 11. The use of a purge gas, such as nitrogen, for cleaning only the vacuum distiller was previously disclosed in Hiatt, M. H., *Analytical Chemistry* 1997, 69, 1127–1134. These changes permit the automatic sampler to be connected to the vacuum distiller condenser column, parts 5–13 of U.S. Pat. No. 5,411,707.

The automatic sampler lines are electronically heated and controlled to a selected temperature between ambient and 200° C., as required by experimental conditions used. The lines of the automatic sampler are heated using heating cable, such as FE12-120B, Omega, Stanton, Conn., placed alongside of the tubing. Heating may be effected using a number of alternatives, such as filaments, heating tapes, or cartridges. The heated cable and lines are preferably wrapped with aluminum foil or other such material to ensure an even distribution of heat. The tubing, valves, and O-ring connectors are optionally placed into ceramic fiber blocks by tier for insulation (Cotronics Corp., Brooklyn, N.Y.).

Referring to FIG. 4, which shows the vacuum extractor of U.S. Pat. No. 5,411,707, one means for regulating the temperature of the fluid flowing through coil 6 is by alternating heating and cooling. Fluid from coil 6 is pumped by pump 108 in the fluid flow direction 107 through line 109 to valve 110 which flows the fluid to either heating means 112 or cooling means 113. Condenser fluid is pumped through line 9 to a valve 10 which flows the fluid to heating means 112 or cooling means 113.

At the opposite end of the condenser of U.S. Pat. No. 5,411,707, is a vacuum pump valve 114, which connects the gas flow to a vacuum pump 115 or connects the flow to a sampling valve 116 through a cryotrap 117 and then via loop 118 to a detection system 121. When the vacuum line connected to loop 118 is disconnected, an inert gas 120 is passed through the cryotrap 117 to revolatalize the compounds to be passed through flow 119 to the detection system 121.

As with the vacuum distiller per se, movement of vapors through the automatic sampler is by volatilization due to lowered pressures. The lower pressure in the automatic samples is caused by the vacuum distiller pump 15 in common with the vacuum distiller. In one embodiment, the automatic sampler is controlled by a microprocessor which is also a component of the vacuum distiller. In this case, the microprocessor is controlled by the analyst on a sample by sample basis. However, the ultimate control of the microprocessor (automatic sampler as well as vacuum distiller) can be programmed from, for example, a Windows NT platform in such a way as to provide total automation of both systems.

The vacuum distiller 101 vacuum distills samples which have been loaded into the automatic sampler. The automatic sampler performs the necessary task of allowing samples to be introduced to the vacuum distiller in predetermined order while allowing the sequence of sampling to be free of contamination by samples loaded onto the automatic sampler for the current group of analyses or previously analyzed in the system.

As described in U.S. Pat. No. 5,411,707, the vacuum distillation-detector system 101 is shown in the loading position. In the original system, the sample is placed into a container, whereas, in the present invention, samples are introduced into sample containers a-1 using the automatic sampler system. The sample chamber, shown in FIG. 4 as 102, is connected to the remainder of the system through a sample valve 103. Air-tight seals 104 can be located on either the sample chamber or the sample chamber valve, and the valve may be removable from both.

The sample chamber valve 103 is fluidly connected to a condenser 105 which contains a coil 106 or other configuration to provide temperature regulation within the condenser. The coil or other means for heating or cooling the condenser may also be external to the condenser to cool or heat it. The coil 106 is hollow with fluid flowing through it. A collection system (not shown) of liquids condensed on the coil or other surfaces in the condenser may be used to withdraw the liquids and/or separate them for subsequent analysis.

Prior to vacuum distillation and subsequent GC/MS analyses, samples must be placed on the automatic sampler. A sample, e.g., 5 ml. of water, is placed into a sample chamber 2 and attached to an automatic sampler port, e.g., a in FIG. 1, at O-ring joint 4 using an O-ring clamp. This cycle can be repeated for 12 samples by attaching a sample to each of the ports a-1. Once the samples have been attached, the analyst identifies the sequence in which the automatic sampler ports are to be used in the vacuum distillation, and programs the microprocessor accordingly. Once the sequence has been programmed, the analyst loads the first sample's port location into the microprocessor and begins the vacuum distillation routine.

Once the vacuum distiller is readied for a distillation to begin (i.e., the temperature of its components are stabilized, a vacuum distillation begins with the microprocessor opening the first sample port by electronically activating a solenoid, e.g., 3. Sample vapors are then drawn from the sample chamber 2, pass through line 5, valve 3, lines 6 and 9, to manifold 7, line 8, and then into the vacuum distiller 102. The vacuum distiller then condenses vapors and transfers the analytes to the GC/MS or other analytical device for quantitation. At the completion of a vacuum distillation, the vacuum distiller and the automatic sampler manifold are decontaminated (short decontamination). The short decontamination routine is performed while the vacuum distillate is being analyzed by the analyzer. The short decontamination consists of an approximately ten minute purge of the vacuum distiller condenser column in which a gas such as nitrogen is allowed to enter the distiller at valve 11 and exit the apparatus at 10. The purge eliminates most material that was condensed on the condenser column during vacuum distillation. After this ten-minute or so purge the system is pressurized for a short time e.g., about 0.05 minutes, with the gas at about 10 psi, while all the sample port valves in the automatic sampler and valve 10 are closed. After this brief pressurization is complete, the system is evacuated via the vacuum distiller for a reasonable length of time, generally from about 0.5 to about 5 minutes. This pressure-evacuation routine is performed several times, generally up to about 25 times, and preferably about 16 times, after which the vacuum distiller is ready for the next sample on the automatic sampler to be vacuum distilled. This routine of vacuum distillation and decontamination can be repeated for all of the samples on the automatic sampler.

A longer decontamination routine for decontaminating the entire system can also be performed using the automatic sample. This longer decontamination routine is performed when all 12 samples have been analyzed and the sample ports are to be decontaminated. This is a discretionary decontamination step that allows elimination of any buildup of contamination due to a low-boiling material in any samples that contaminate the sample ports. All sample chamber valves may be opened at the same time in order to purge all sample parts of any contamination that may remain following a series of vacuum distillations. During this routine, new sample chamber vessels, or simplified versions of sample chambers, are attached at the sample chamber seals 4 at each sample port to be decontaminated. As with the short decontamination routine, the system is pressurized with gas and is then evacuated via the vacuum distiller vacuum pump. In a series of pressurization and evacuation steps, the automatic sampler is decontaminated when necessary. This routine can be modified for many cycles overnight, if desired.

The automatic sampler was installed in a vacuum distiller/GC/MS system. The heating cables heated the lines to 90° C. by means of power controllers. After the temperatures were stabilized, initial analyses were conducted to test the operation of the automatic sampler. There was no significant variation between results where the sample was introduced through one of the sample ports of the automatic sampler from results where the sample was introduced directly to the sample port of the vacuum distiller operating by itself prior to installation of the automatic sampler. It was also determined that sample distillation times and vacuum distiller settings required no changes after installation of the automatic sampler.

In order to verify the accuracy of the automatic sampler, the "memory" of compounds previously analyzed by the system was evaluated. The memory is defined herein as the percentage of a particular compound that was seen in a blank following the analysis of a standard. The short decontamination routine was perform between samples. Table 1 shows the memory effects determined for a suite of deuterated surrogate compounds. These values were far lower than had been expected, and were lower than memory effects observed on an older single-port vacuum distiller. This level of memory is insignificant for most applications because it is near the detection limits for the compounds. For example, one of the most difficult compounds to clear, naphthalene, the memory effect from a 100 ppb standard is calculated to be 0.8 ppb (0.77%), while the reported minimum detection limit (MDL) is 0.6 ppb. Similarly, it requires a toluene concentration of 2250 ppb in a sample, which far exceeds toluene's normal upper calibration limit. To produce a memory effect in excess of the MDL of toluene of 0.9 ppb (0.04%). Table 1. Percent residue of chemicals in sample ports following a vacuum distillation

| CHEMICAL | % |
|---|---|
| methylene chloride-d6 | 0.04 |
| hexafluorobenzene | 0.01 |
| pentafluorobenzene | 0.00 |
| benzene-d6 | 0.01 |
| 1,2-dichloroethane-d4 | 0.09 |

-continued

| CHEMICAL | % |
|---|---|
| Fluororbenzene | 0.02 |
| 1,4-difluorobenzene | 0.00 |
| 1,2-dichloropropane | 0.07 |
| toluene-d8 | 0.04 |
| 1,1,2-trichloroethane-d3 | 0.01 |
| 1,2-dibromoethane-d4 | 0.09 |
| chlorobenzene-d5 | 0.06 |
| o-xylene-d10 | 0.09 |
| 4-bromofluorobenzene | 0.06 |
| bromobenzene-d5 | 0.10 |
| 1,2-dichlorobenzene-d4 | 0.11 |
| decafluorobiphenyl | 0.53 |
| 1,2,4-trichlorobenzene-d3 | 0.46 |
| naphthalene-d8 | 0.77 |

The foregoing description of the specific embodiments will so fully reveal the general nature of the invention that others can, by applying current knowledge, readily modify and/or adapt for various applications such specific embodiments without departing from the generic concept, and, therefore, such adaptions and modifications should and are intended to be comprehended within the meaning and range of equivalents of the disclosed embodiments. It is to be understood that the phraseology or terminology employed herein is for the purpose of description and not of limitation.

What is claimed is:

1. A method for sequentially analyzing a plurality of samples comprising:
   a. introducing said plurality of samples into an automatic sampler, wherein said automatic sampler comprises a plurality of sample ports connected with a sample holder, a connector, a valve, and a seal, the connector of each sample holder being attached to the valve by a transfer line, wherein each sample port is connected to a common manifold;
   b. activating a vacuum pump to volatilize the samples sequentially through the common manifold to a vacuum distiller, wherein the order in which the samples are volatilized is controlled by a microprocessor; and
   c. condensing the vapors produced by the vacuum distiller and transferring the condensed vapors to an analytical device.

2. The method according to claim 1 wherein the transfer lines are heated.

3. The method according to claim 1 wherein after the condensed vapors from a sample are transferred to the analytical device, the automatic sampler is decontaminated with a purge gas while all of the sample port valves are closed and the system is evacuated via the vacuum distiller.

4. The method according to claim 3 wherein the decontamination step is repeated up to about 25 times.

5. The method according to claim 1 wherein, after all of the samples have been analyzed, all of the sample valves are opened, the automatic sampler is purged with an inert gas, and the automatic sampler is evacuated via the vacuum distiller pump.

6. In a method for vacuum distillation of samples, the improvement comprising introducing the samples into an automatic sampler, said automatic sampler comprising:
   a. a plurality of sample containers;
   b. a plurality of sample ports;

c. means for fluidly connecting the sample containers through the sample ports to an analyzer, said means including a vacuum distiller and a vacuum pump which evaporates the sample, condenses the sample, and transfers the condensed fluid to an analytical device; and d. a microprocessor for sequencing the order of sampling.

7. The method according to claim 6 wherein the automatic sampler further contains a purge gas line for cleaning the analyzer between samplings.

8. The method according to claim 6 wherein the automatic sampler further comprises means to control the temperature in lines in the sampling device.

9. The method according to claim 6 wherein in the automatic sampling apparatus the sample ports are arranged in horizontal tiers and a manifold comprises a vertical tube that connects the horizontal tiers of sample ports.

10. The method according to claim 6 wherein the sample ports in the automatic sampling device comprise a container for a sample with a connector, a valve, and a seal, wherein each connector is attached to the valve by a transfer line, which is connected to a manifold.

* * * * *